(12) United States Patent
Ohbi

(10) Patent No.: US 8,129,474 B2
(45) Date of Patent: Mar. 6, 2012

(54) SEAL FOR A DISPENSING APPARATUS

(75) Inventor: Daljit Ohbi, Norfolk (GB)

(73) Assignee: Consort Medical PLC, Hemel Hempstead, Hertfordshire (GB)

( * ) Notice: Subject to any disclaimer, the term of this patent is extended or adjusted under 35 U.S.C. 154(b) by 964 days.

(21) Appl. No.: 11/817,448

(22) PCT Filed: Mar. 3, 2006

(86) PCT No.: PCT/GB2006/000772
§ 371 (c)(1),
(2), (4) Date: Apr. 16, 2008

(87) PCT Pub. No.: WO2006/092618
PCT Pub. Date: Sep. 8, 2006

(65) Prior Publication Data
US 2008/0230567 A1    Sep. 25, 2008

(30) Foreign Application Priority Data
Mar. 4, 2005    (GB) .................................. 0504565.3

(51) Int. Cl.
*A61J 1/00*    (2006.01)

(52) U.S. Cl. ...................................................... 525/240

(58) Field of Classification Search ............. 222/402.24, 222/402.2, 402.1; 525/191, 203, 209, 210, 525/217, 232, 240, 241; 524/445, 451, 492, 524/515, 525
See application file for complete search history.

(56) References Cited

U.S. PATENT DOCUMENTS

| | | | |
|---|---|---|---|
| 3,499,584 A | | 3/1970 | Warren |
| 5,290,539 A | | 3/1994 | Marecki |
| 5,836,299 A | | 11/1998 | Kwon |
| 6,092,696 A | | 7/2000 | Thomas |
| 6,310,140 B1 | | 10/2001 | Raetzsch et al. |
| 6,642,316 B1 * | | 11/2003 | Datta et al. ................... 525/240 |
| 6,943,215 B2 | | 9/2005 | Stevens et al. |
| 7,041,765 B2 | | 5/2006 | Tau et al. |
| 7,411,017 B2 * | | 8/2008 | Imai ............................ 524/525 |
| 7,855,258 B2 * | | 12/2010 | Datta et al. ................... 526/160 |
| 2004/0087751 A1 | | 5/2004 | Tau et al. |
| 2004/0129737 A1 | | 7/2004 | Anderson et al. |
| 2006/0183861 A1 | | 8/2006 | Harrington et al. |
| 2006/0273117 A1 | | 12/2006 | Barranco et al. |

FOREIGN PATENT DOCUMENTS

| | | |
|---|---|---|
| EP | 1591482 | 11/2005 |
| FR | 2549568 A3 | 1/1985 |
| GB | 1566239 | 4/1980 |
| GB | 2148912 A | 6/1985 |
| GB | 2410500 | 8/2005 |
| WO | 9211190 | 7/1992 |

(Continued)

OTHER PUBLICATIONS

Abstract of WO9919235; Apr. 22, 1999.

(Continued)

*Primary Examiner* — Kevin P Shaver
*Assistant Examiner* — Donnell Long
(74) *Attorney, Agent, or Firm* — Senniger Powers LLP

(57) ABSTRACT

A seal for a valve for use in a pharmaceutical dispensing device, which seal is formed from a thermoplastic elastomer including a propylene component with isotactic crystallinity.

24 Claims, 8 Drawing Sheets

FOREIGN PATENT DOCUMENTS

Figure 1:
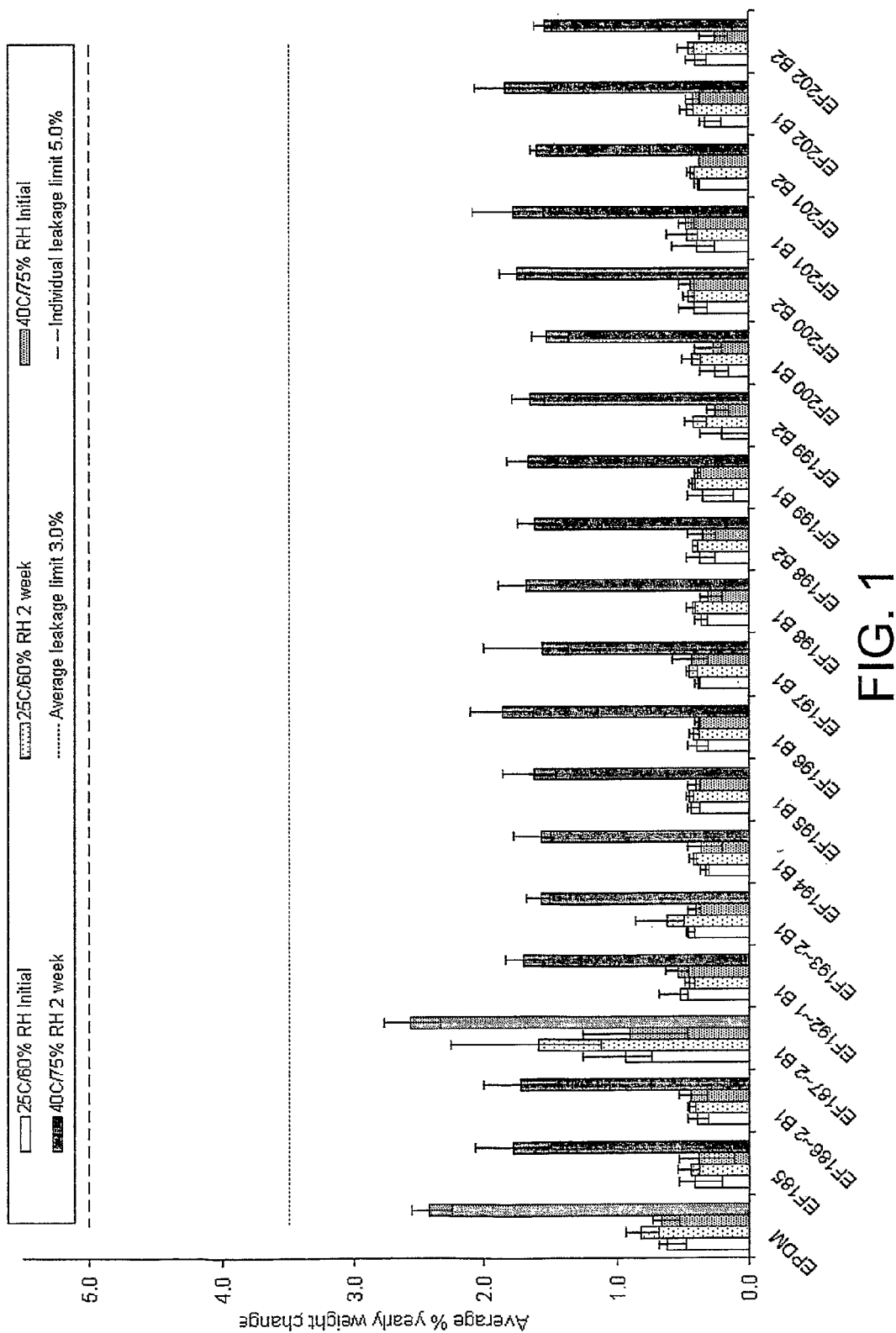

| | | |
|---|---|---|
| WO | 9322221 | 11/1993 |
| WO | 9502651 | 1/1995 |
| WO | 9503984 | 2/1995 |
| WO | 9701611 | 1/1997 |
| WO | 9919235 | 4/1999 |
| WO | 9920664 | 4/1999 |
| WO | 2005010413 A2 | 2/2005 |

OTHER PUBLICATIONS

International Search Report, PCT/GB2006/000772, dated Mar. 20, 2006, 2 pages.
Abstract of FR2549568; Jan. 25, 1985.

* cited by examiner

SEAL FOR A DISPENSING APPARATUS

The present invention relates to a seal material and, in particular, to a seal material comprising a polyolefin thermoplastic elastomer. The seal may be used for dispensing pressurised fluid in the form of an aerosol. The seal is particularly suitable for use in pressurised metered dose aerosol inhaler devices (pMDIs) and in medical check devices suitable for dispensing a pharmaceutical. The seal may be used also in pumps and nasal delivery devices.

It is known from GB 1201918 for example to provide dispensing apparatus in which pressurised fluid from a pressurised dispensing container is released by a valve in a controlled manner, the valve including elastomeric seals which are annular and which co-operate with a sliding valve stem to open and close fluid ports. FR-A-2,549,568, WO95/02651 and GB 2,148,912 and PCT/GB96/01551 each disclose further examples of such dispensing apparatus.

The required material properties necessary for good seal performance for pharmaceutical applications include: chemical compatibility (swell), tensile strength, permanent compression set, stress relaxation, elastic modulus, regulatory compliance, low permeability to fluids and gases, low levels of extractables and leachables, and stable properties after extraction.

Accordingly, as well as the requirement for good engineering properties, there is a requirement for sanitary properties, including low levels of extractables and leachables, which might otherwise increase impurities of drug products to unacceptable levels, as well as potentially reacting with the drug product, vehicle or excipients. In this connection, products to be dispensed by the pMDI are commonly provided in solution or suspension in an alcohol base, this being particularly common in the dispensing of medicinal compounds for inhalation therapy.

The metering valves used in dispensing devices such as pMDIs are typically constructed from a mixture of metal and/or thermoplastic parts and elastomeric rubber parts. The seal itself typically comprises an elastomer such as a synthetic rubber, for example, nitrile rubber.

It is known from WO 00/40479 to use a two-phase elastomeric alloy material for a regulating member in an aerosol valve and flow regulator assembly.

The benefits of using "alloyed" or "blended" materials include high elasticity and low hardness. For example, favourable values of elasticity and Shore Hardness (A) can be achieved when a softer elastomeric component is dispersed in a matrix of a thermoplastic material.

The production of seals comprising elastomeric materials typically involves steps for the curing/cross-linking of natural and synthetic rubbers. Accelerators are compounds which reduce the time required for curing/cross-linking of natural and synthetic rubbers. Examples include sulphur-based compounds. Accelerators may also act to improve the non-permeability characteristics and other physical properties of the rubber.

Peroxides such as dicumyl peroxide can also be used to cure elastomers. However, the curing reaction can be variable and this may affect the material properties; in extreme cases, the material can become brittle. Moreover the products of the reaction have to be removed as they can deteriorate elastomer properties, for example ageing. Another problem is that peroxides are deactivated by antioxidants. Antioxidants are often required to enhance the ageing properties of the elastomer.

The pMDI devices containing propellant and drug mixtures are pressurised at ambient temperatures typically up to 5 bar (500 kPa). Under these conditions the residual by-products from the curing/cross-linking reaction can migrate out and interfere with the drug mechanisms.

Accordingly, in most pharmaceutical applications it is also necessary to extract or wash the cured elastomer in order to remove surface residues and by-products resulting from the cure reaction and moulding process. Examples include ethanol and super-critical fluid extraction. Prolonged extraction times have been found, however, to result in a deterioration in material properties. Moreover, extraction processes add to production costs.

It is an object of the present invention to provide a seal material for a dispensing apparatus which addresses at least some of the problems associated with the prior art.

Accordingly, in a first aspect, the present invention provides a seal for a valve for use in a pharmaceutical dispensing device, which seal is formed from a thermoplastic elastomer including a propylene component with isotactic crystallinity.

The seal according to the present invention is formed from a material comprising a polyolefin thermoplastic elastomer with isotactic propylene crystallinity.

The term seal as used herein is intended to encompass any sealing member or portion thereof present in a pharmaceutical dispensing device, including, but not limited to, gaskets, seats and seals, whether static or dynamic.

It will be appreciated that the seal may be provided as a separate component or may be formed integrally with the valve, i.e. be co-moulded.

The polyolefin thermoplastic elastomer preferably comprises a copolymer or terpolymer of propylene and one or more alpha-olefins. The alpha-olefin is preferably selected from one or more of ethylene, butene, hexene, octene, and decene.

The polyolefin thermoplastic elastomer preferably comprises propylene with from 2 to 25% isotactic crystallinity, more preferably from 5 to 15% isotactic crystallinity, still more preferably from 5 to 10% isotactic crystallinity.

The polyolefin thermoplastic elastomer preferably comprises at least 80% propylene co-monomer, more preferably at least 85% propylene co-monomer. The polyolefin thermoplastic elastomer is preferably semi-crystalline.

The polyolefin elastomer preferably has a molecular weight (Mw) of at least 100,000, more preferably at least 130,000. The Mw/Mn is preferably from 1.5 to 2.5, more preferably approximately 2.

The preferred polyolefin elastomer comprises a copolymer of propylene and other alpha-olefins, preferably one of which is ethylene. The ratio of propylene is at least 80%.

The isotactic propylene is preferably a linear-substituted hydrocarbon polymer in which all or substantially all of the substituent groups lie on the same side of the carbon chain. The polymer is preferably highly stereo-regular.

Semicrystalline co- and ter-polymers of propylene and other alpha-olefins are preferred, preferably containing at least 80% propylene with isotactic stereochemistry. The polymer preferably exhibits a substantially uniform intermolecular/intramolecular distribution of composition and crystallinity.

A preferred example of the polyolefin elastomer is Vistamaxx (RTM), which is manufactured by the Exxon Mobil Chemical Company. A polyolefin elastomer is also available from Dow under the name Versify (RTM).

The inventors have found that a copolymer or terpolymer of propylene and an alpha-olefin can effectively be used in alloys or blends with other polymers and/or fillers to produce materials that function as effective sealing materials in pMDI devices. Accordingly, the seal material preferably further comprises one or more additional thermoplastic components such as, for example, polymers selected from styrene-ethylene-ethylene-propylene, styrene-ethylene-propylene, styrene-butadiene-styrene, polyether block polyamide, polyether-polyester, ethylene-diene, polydimethylsiloxane/urea copolymers, and/or cyclo-olefin copolymers, including combinations of two or more thereof. The one or more additional thermoplastic components is/are typically present in the seal material in an amount of from 1 to 40 wt. %, preferably from 1 to 10 wt. %, still more preferably from 1 to 5 wt. %.

The weight ratio of the one or more additional thermoplastic components to the polyolefin thermoplastic elastomer is preferably in the range of from 1:99 to 40:60.

The seal material preferably further comprises a mineral and/or inorganic filler. Mineral fillers are preferable to carbon black in order to minimise the formation of polynuclear aromatic hydrocarbon compounds. Suitable examples include any of magnesium silicate, aluminium silicate, silica, titanium oxide, zinc oxide, calcium carbonate, magnesium oxide magnesium carbonate, magnesium aluminium silicate, aluminium hydroxide, talc, kaolin and clay, including combinations of two or more thereof. Preferably, the filler is or comprises one or more of magnesium silicate, talc, calcined clay, nano particle clays, kaolin and/or amino silane coated clay or clay coated with a titanium or zirconate coupling agent. The filler is typically present in the seal material in an amount of from 1 to 40 wt. %, preferably from 1 to 30 wt. %, more preferably from 1 to 20 wt. %, still more preferably from 1 to 10 wt. %.

The seal material preferably comprises both an additional thermoplastic component as herein described and a mineral/inorganic filler as herein described.

The polymer alloys, mixtures or blends may be produced by conventional methods, for example using a twin-screw mixer extruder or by injection moulding. Thus, the seal may be produced by a process involving: providing a composition comprising a polyolefin thermoplastic elastomer with propylene crystallinity and optionally one or more additional thermoplastic components and optionally one or more fillers as herein described; and forming the composition into a seal. In this process the step of forming the composition into a seal may involve one or more forming techniques such as compression moulding, injection moulding and/or extrusion. The seal material according to the present invention lends itself particularly to injection moulding and this is advantageous because it reduces manufacturing cycle times from minutes (6-10 minutes for compression/transfer moulding) to seconds (15-25 seconds for injection moulding). Injection moulding also results in reduced process waste compared to compression/transfer processes. The seal can also be co-moulded if desired with thermoplastics such as PBT, nylon and/or polyacetal.

The inventors have found that alloying or blending of semi-crystalline propylene co- or ter-polymers with inorganic/mineral fillers and/or thermoplastic components has yielded compositions with elastomeric properties suitable for sealing applications in pharmaceutical applications. It has surprising been found that this can be achieved without the use of plasticisers or processing aids or compatibilising agents, which are typically required for producing alloys/blends. Thus, the present invention enables a seal material to be produced that is essentially free of a cross-linking agent if desired. The seal material may also be essentially free of a plasticizer. The seal material may also be essentially free of a processing aid. The seal material may also be essentially free of a compatiblising agent.

In a preferred embodiment, the present invention provides a seal for a valve for use in a pharmaceutical dispensing device, which seal is formed from a material consisting of or consisting essentially of:

a polyolefin thermoplastic elastomer including a propylene component with semi-crystallinity, preferably a copolymer of propylene and an alpha-olefin;

optionally one or more additional thermoplastic components as herein described; and optionally one or more mineral and/or inorganic fillers as herein described; and any unavoidable impurities.

The seal material according to the present invention is very clean having extractible levels of typically 8 to 500 ppm (by GC-MS).

The seal material according to the present invention also has good sealing characteristics, which are comparable to those of conventional EPDM and nitrile elastomers. Surprisingly the elastomeric properties of the seal material are maintained at elevated conditions, for example 40° C./75% RH.

Although not essential, if desired, the seal material may further comprise any of a reinforcement agent, processing aid, a plasticizer, a binder, a stabilizer, a retarder, a bonding agents, an antioxidant, a lubricant, a pigment, a wax, a resin, an antiozonants, a secondary accelerator or an activator, including combinations of two or more thereof. Examples of antioxidants are 2:2'-methylene-bis(6-(1-methyl-cyclohexyl)-para-creosol) and octylated diphenylamine.

As mentioned above, a benefit of using a seal in accordance with the present invention in a pharmaceutical dispensing device is the relatively low levels of leachables and extractables that are present. Thus, while seals prepared according to the present invention may be ethanol extracted (i.e. washed by refluxing ethanol) to reduce the level of any leachable species that could migrate into drug mixtures, this step is not essential and can be dispensed with. This is in contrast to conventional thermoset rubbers, which do require an ethanol extraction. As mentioned above, the seal material according to the present invention has extractible levels of typically 8 to 500 ppm (by GC-MS). It will be appreciated that the extractible levels may be further reduced, if required, by performing an extraction step.

The seal according to the present invention may be used in a valve for use in a dispensing device, such as, for example, a nasal, pulmonary or transdermal delivery device. Preferred uses of the seal are in a pressurised metered dose aerosol inhaler device and in a medical check device suitable for dispensing a pharmaceutical.

The term pharmaceutical as used herein is intended to encompass any pharmaceutical, compound, composition, medicament, agent or product which can be delivered or administered to a human being or animal, for example pharmaceuticals, drugs, biological and medicinal products. Examples include antiallergics, analgesics, bronchodilators, antihistamines, therapeutic proteins and peptides, antitussives, anginal preparations, antibiotics, anti-inflammatory preparations, hormones, or sulfonamides; such as, for example, a vasoconstrictive amine, an enzyme, an alkaloid, or a steroid, including combinations of two or more thereof. In particular, examples include isoproterenol [alpha-(isopropylaminomethyl) protocatechuyl alcohol], phenylephrine, phenylpropanolamine, glucagon, adrenochrome, trypsin, epinephrine, ephedrine, narcotine, codeine, atropine, heparin, morphine, dihydromorphinone, ergotamine, scopolamine, methapyrilene, cyanocobalamin, terbutaline, rimiterol, salbutamol, flunisolide, colchicine, pirbuterol, beclomethasone, orciprenaline, fentanyl, and diamorphine, streptomycin, penicillin, procaine penicillin, tetracycline, chlorotetracycline and hydroxytetracycline, adrenocorticotropic hormone and adrenocortical hormones, such as cortisone, hydrocortisone, hydrocortisone acetate and prednisolone, insulin, cromolyn sodium, and mometasone, including combinations of two or more thereof.

The pharmaceutical may be used as either the free base or as one or more salts conventional in the art, such as, for example, acetate, benzenesulphonate, benzoate, bicarbonate, bitartrate, bromide, calcium edetate, camsylate, carbonate, chloride, citrate, dihydrochloride, edetate, edisylate, estolate, esylate, fumarate, fluceptate, gluconate, glutamate, glycollylarsanilate, hexylresorcinate, hydrobromide, hydrochloride, hydroxynaphthoate, iodide, isethionate, lactate, lactobionate, malate, maleate, mandelate, mesylate, methylbromide, methylnitrate, methylsulphate, mucate, napsylate, nitrate, pamoate, (embonate), pantothenate, phosphate, diphosphate, polygalacturonate, salicylate, stearate, subacetate, succinate, sulphate, tannate, tartrate, and triethiodide, including combinations of two or more thereof. Cationic salts may also be used, for example the alkali metals, e.g. Na and K, and ammonium salts and salts of amines known in the art to be pharmaceutically acceptable, for example glycine, ethylene diamine, choline, diethanolamine, triethanolamine, octadecylamine, diethylamine, triethylamine, 1-amino-2-propanol-amino-2-(hydroxymethyl)propane-1,3-diol, and 1-(3,4-dihydroxyphenyl)-2 isopropylaminoethanol.

The pharmaceutical will typically be one which is suitable for inhalation and may be provided in any suitable form for this purpose, for example as a powder or as a solution or suspension in a solvent or carrier liquid, for example ethanol.

The pharmaceutical may, for example, be one which is suitable for the treatment of asthma. Examples include salbutamol, beclomethasone, salmeterol, fluticasone, formoterol, terbutaline, sodium chromoglycate, budesonide and flunisolide, and physiologically acceptable salts (for example salbutamol sulphate, salmeterol xinafoate, fluticasone propionate, beclomethasone dipropionate, and terbutaline sulphate), solvates and esters, including combinations of two or more thereof. Individual isomers such as, for example, R-salbutamol, may also be used. As will be appreciated, the pharmaceutical may comprise of one or more active ingredients, an example of which is flutiform, and may optionally be provided together with a suitable carrier, for example a liquid carrier. One or more surfactants may be included if desired.

According to a second aspect, the present invention also provides a pharmaceutical dispensing device having a valve as herein described. The pharmaceutical dispensing device may be, for example, a nasal, pulmonary or transdermal delivery device. Preferred devices are a pharmaceutical metered dose aerosol inhaler device and a medical check device.

The present invention also provides a dispensing apparatus for dispensing pressurised fluid comprising a valve body defining a chamber, a valve member extending movably through the chamber and through at least one annular seal co-operating with the valve member and the body to regulate the discharge of fluid, wherein the or at least one of the seals is as herein described with reference to the first aspect of the invention.

Such a device may be used for dispensing medicine, pharmaceuticals, biological agents, drugs and/or products in solution or suspension as herein described.

In a preferred embodiment, the dispensing apparatus comprises a pressurised dispensing container having a valve body provided with two annular valve seals through which a valve member is axially slidable, the seals being disposed at inlet and outlet apertures of a valve chamber so that the valve functions as a metering valve.

The dispensing apparatus as herein described may comprise a pressurised dispensing container operatively connected to the valve body and containing the fluid to be dispensed and a hydrofluorocarbon propellant comprising propellant type 134a or 227. The designation of propellant types referred to in the present application is as specified in British Standard BS4580:1970 "Specification for number designations of organic refrigerants". Accordingly, propellant 134a is: 1,1,1,2-tetrafluoroethane CH2F—CF3 and propellant 227 is: 1,1,1,2,3,3,3 heptafluoropropane CF3—CHF—CF3.

The fluid to be dispensed typically comprises a liquid or particulate product as a solution or suspension in a carrier liquid. The carrier liquid preferably comprises an alcohol such as ethanol. One or more surfactants may be present.

EXAMPLES AND FIGURES

The present invention will now be described further with reference to the following non-limiting examples in Tables 1 to 3 and FIGS. 1 to 8.

Table 1 lists a number of thermoplastic elastomer compositions in accordance with the present invention. Table 2 lists the physical properties of these compositions. Table 3 gives the results of GC-MS analysis on the thermoplastic elastomer compositions in accordance with the present invention and also GC-MS Analysis of a conventional non-ethanol extracted EPDM rubber and a conventional non-ethanol extracted nitrile rubber.

FIG. 1 shows the leakage characteristics of the seal compositions at 25° C./60% RH and 40° C./75% RH using HFA 134a+10% ethanol. Data for a conventional EPDM rubber seal is also provided for comparison. The compositions meet the USP26 <601> leakage test requirements for aerosols. The limits are based upon the USP26 <601> leakage test requirements for aerosols. The requirements are met if the average leakage rate per year is not more than 3.5% of the net fills weight, and none of the containers leaks more than 5.0% of the net fill weight per year. It is apparent that at elevated test conditions the compositions (except for EF187~2 B1) exhibit lower leakage than the EPDM control.

Figure 2:
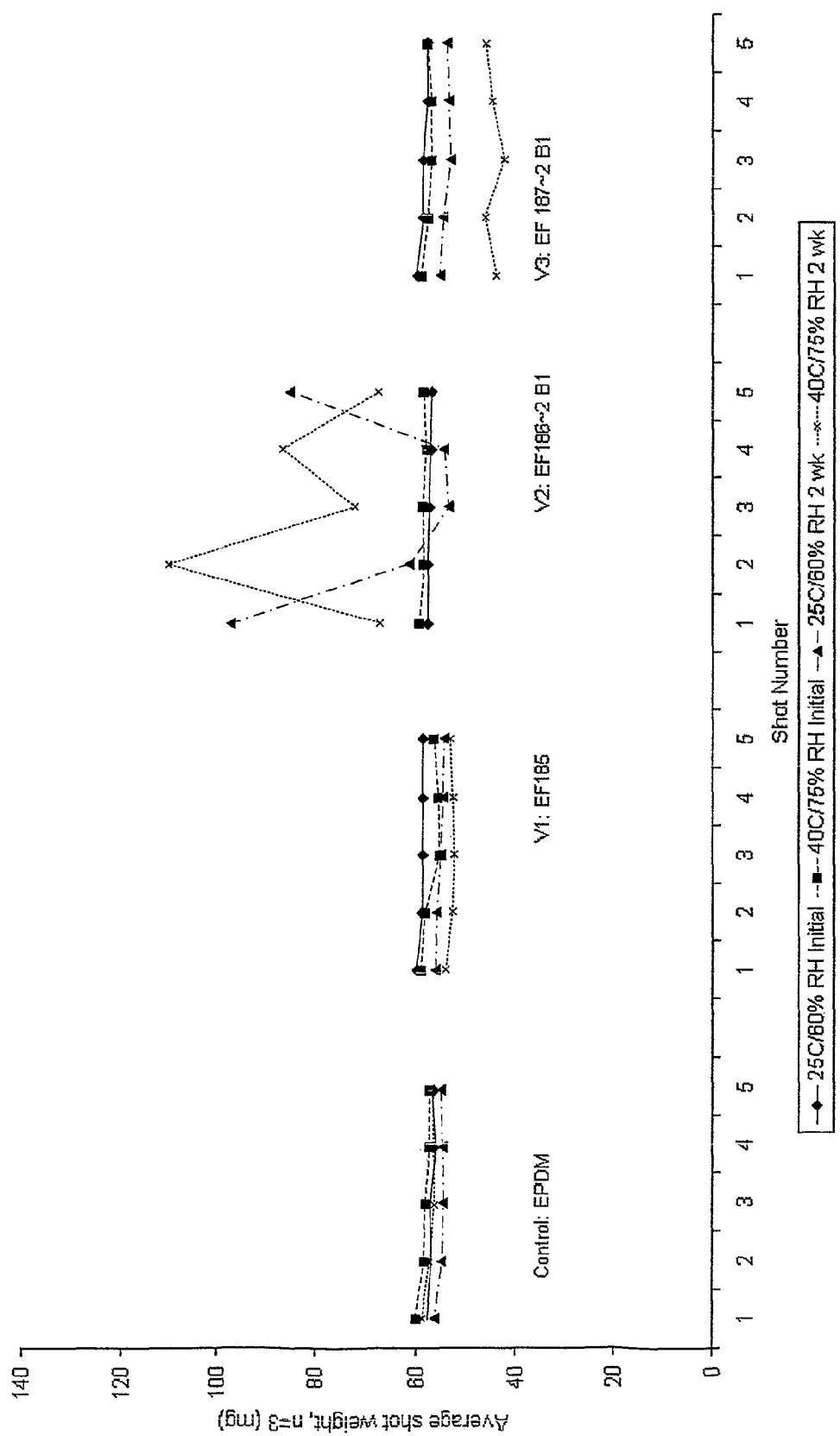
Figure 3:
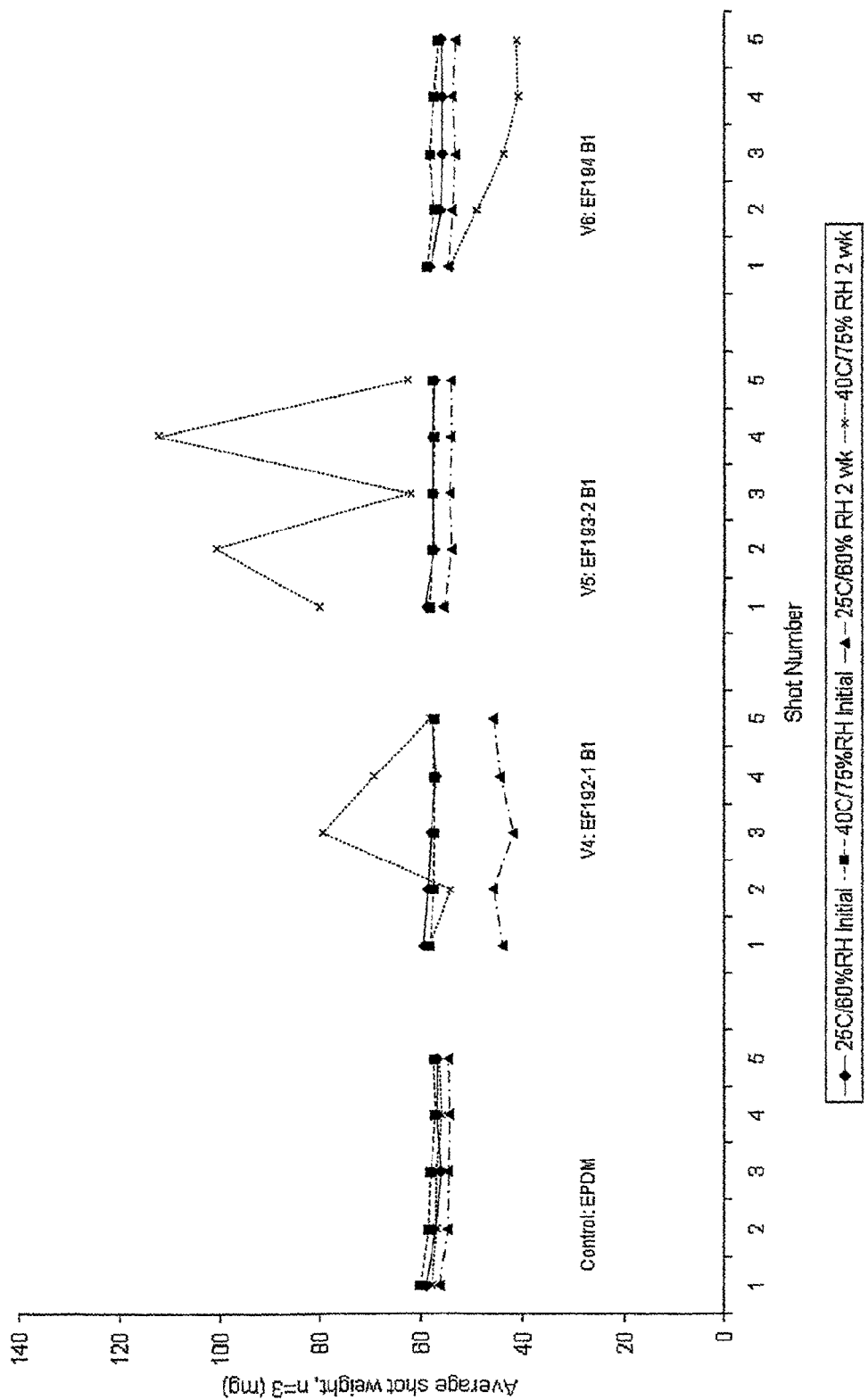
Figure 4:
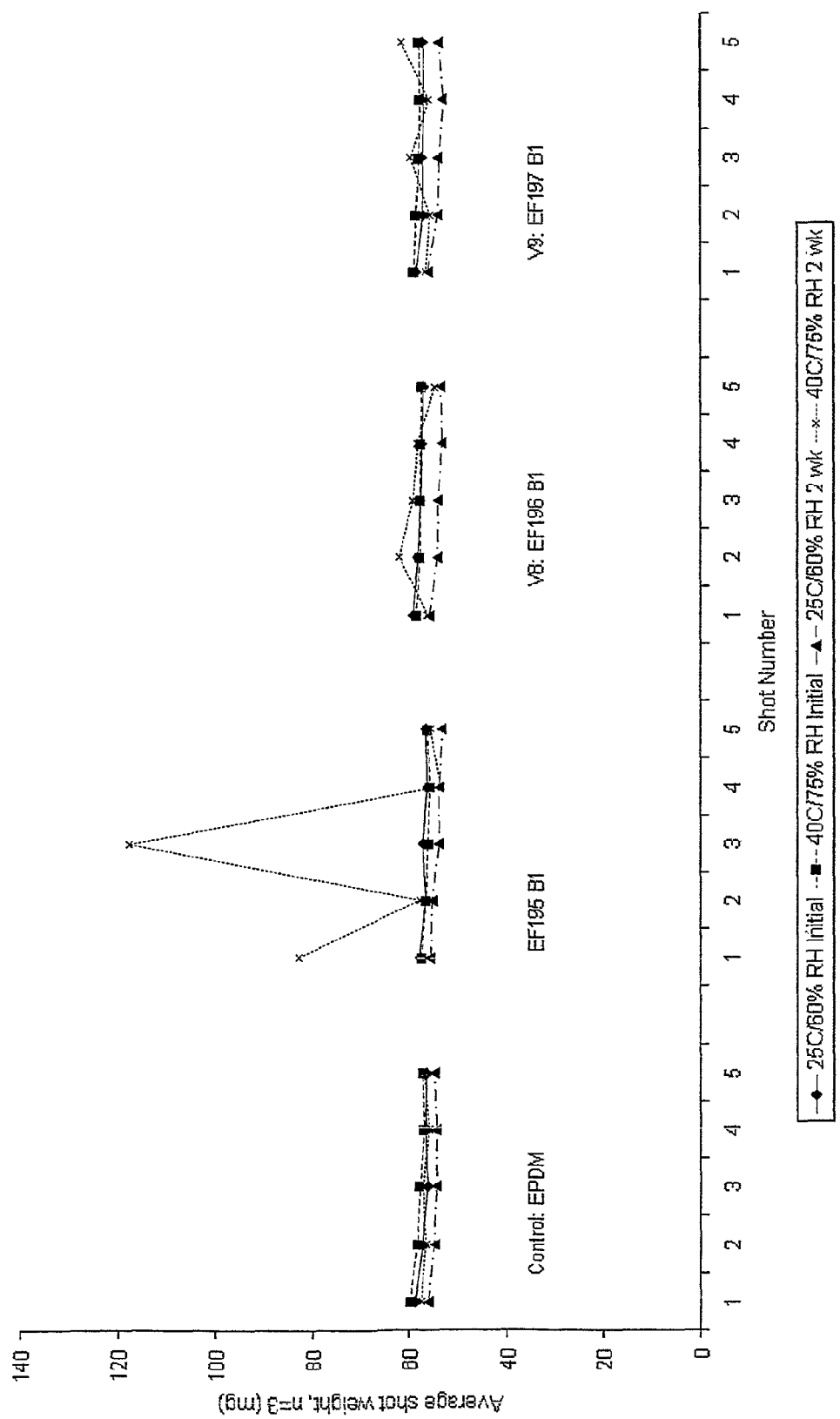
Figure 5:
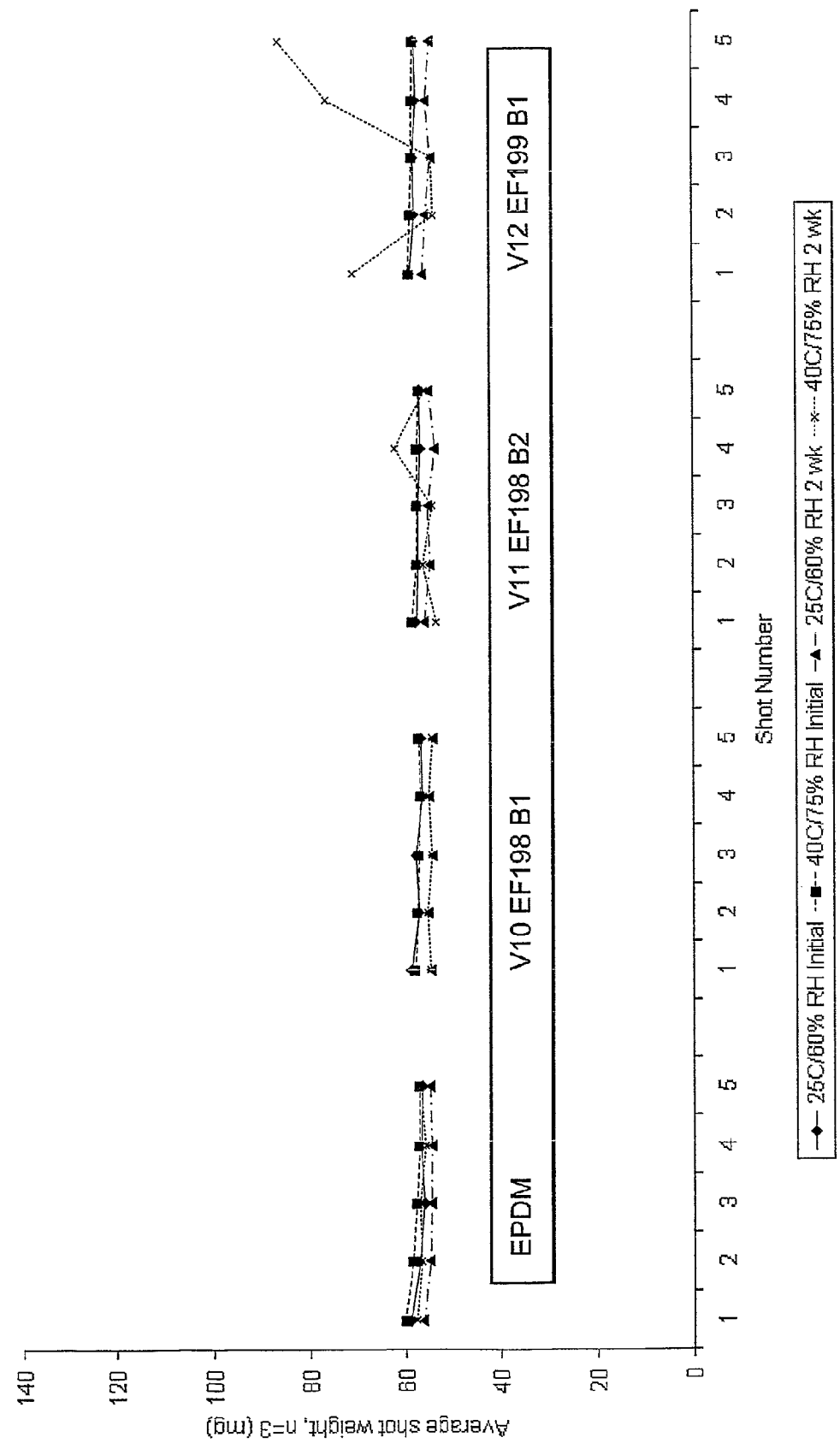
Figure 6:
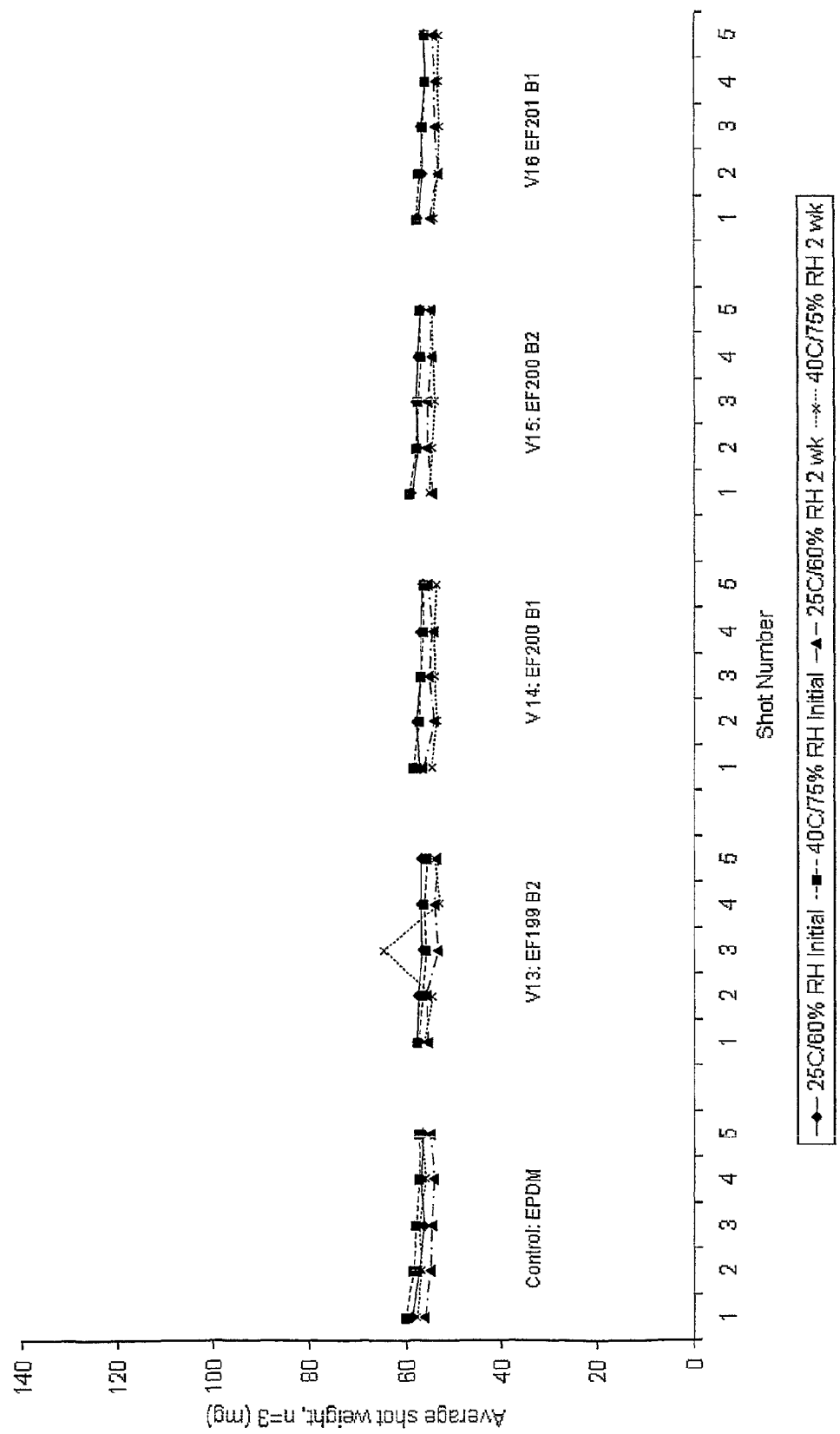
Figure 7:
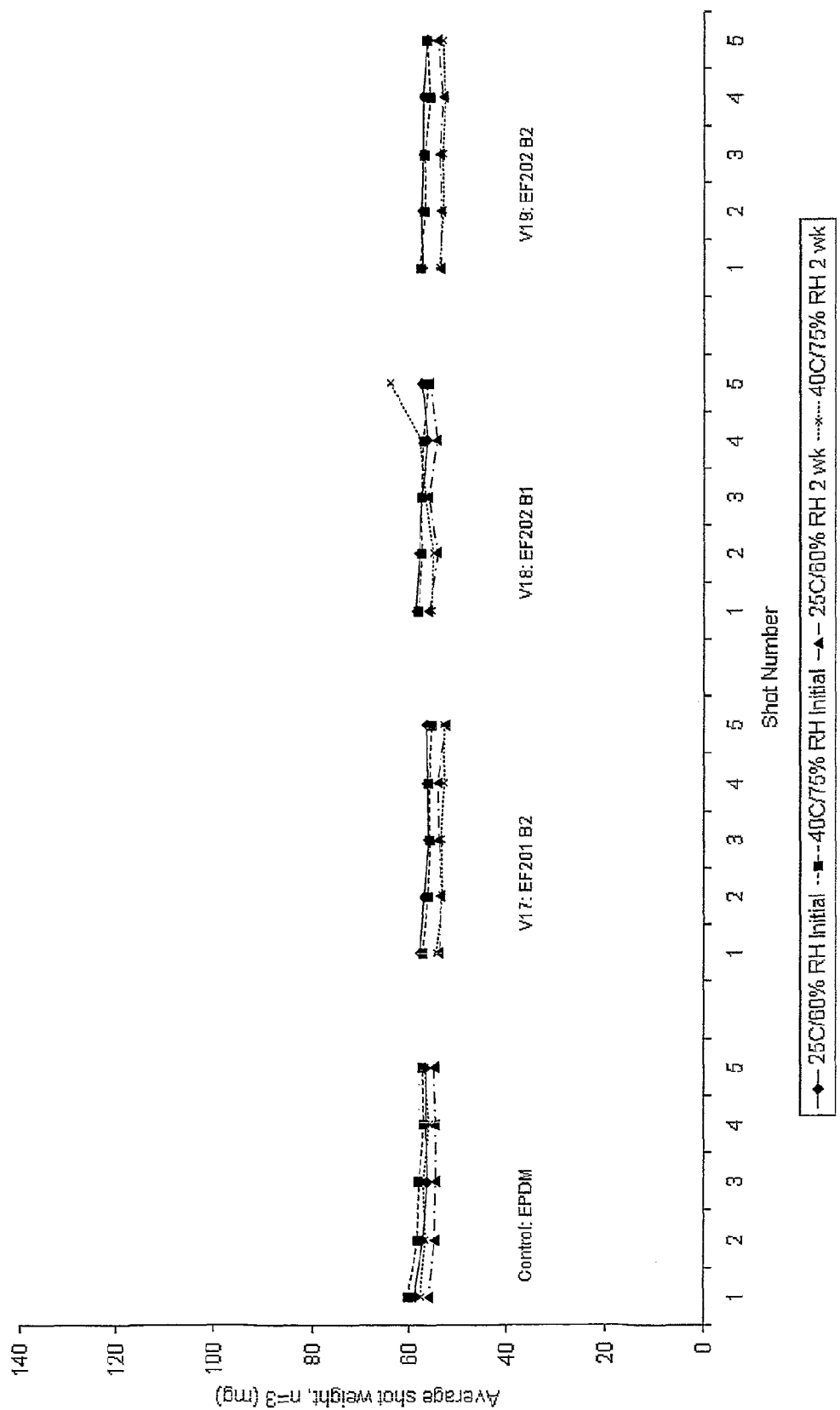

The shot weight performance of the seal compositions is given in FIGS. 2-7. The performance of a conventional EPDM rubber seal is included for comparison. The shot weight performance was determined from 3 samples of each Alloy variation. The packs were filled with HFA 134a+10% ethanol, each pack was fired 5 times. FIG. 2 compares the shot weight performance of Alloys EF185, EF186~2 B1 and EF187~2 B2 with the EPDM control. FIG. 3 compares the shot weight performance of Alloys EF192~1 B1, EF193~2 B1 and EF194 B1 with the EPDM control. FIG. 4 compares the shot weight performance of Alloys EF195 B1, EF196 B1 and EF197 with the EPDM control. FIG. 5 compares the shot weight performance of Alloys EF198 B1, EF198 B2 and EF199 B1 with the EPDM control. FIG. 6 compares the shot weight performance of Alloys EF199 B2, EF200 B1, EF200 B2 and EF201 B1 with the EPDM control. FIG. 7 compares the shot weight performance of Alloys EF201 B2, EF202 B1 and EF202 B2 with the EPDM control.

Figure 8:
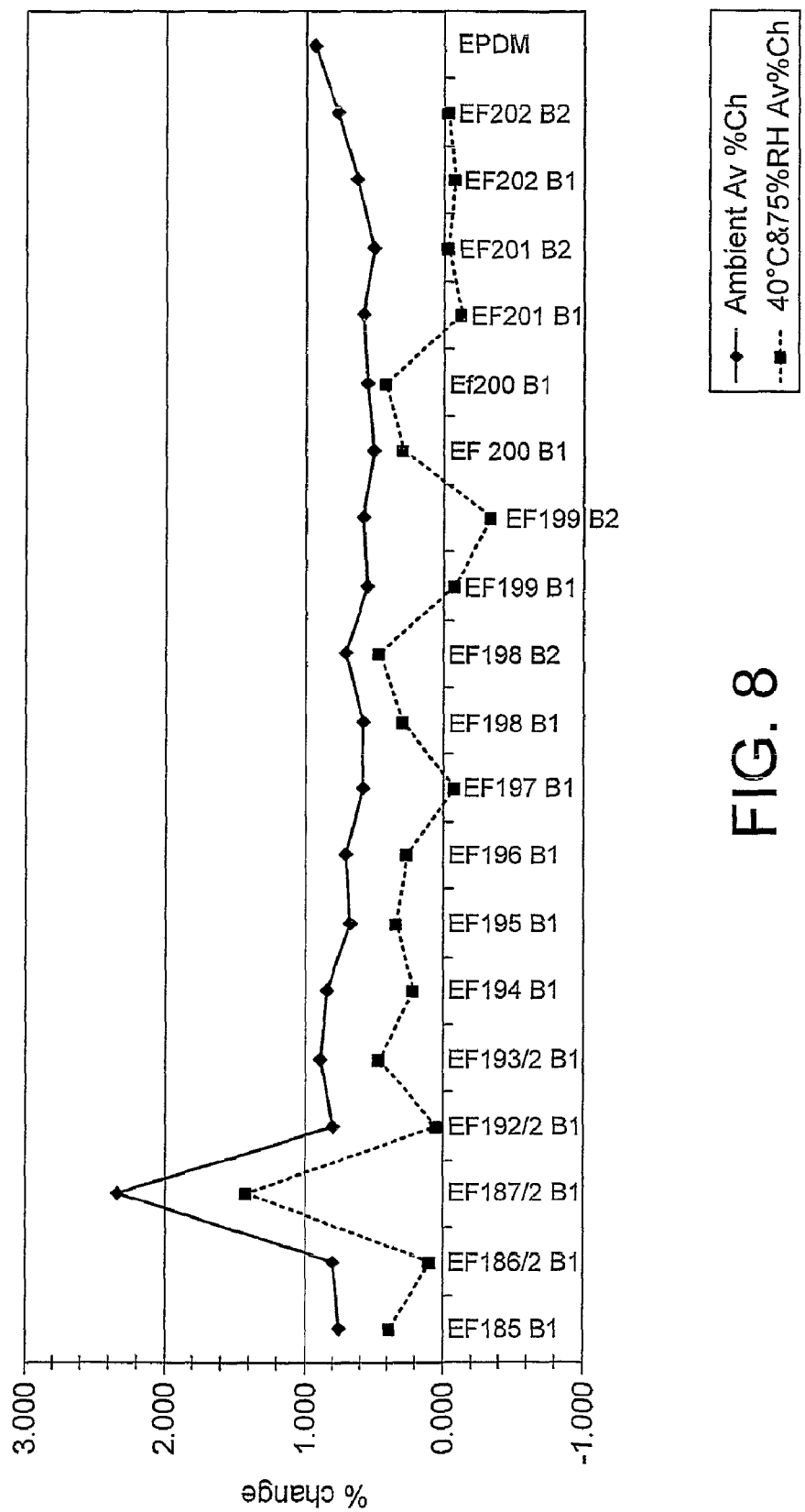

The swelling characteristics of the seal compositions in HFA 134a+10% ethanol at ambient is given in FIG. 8. The change in the diameter of the seals was calculated after 7 day immersion at ambient. The performance of a conventional EPDM rubber seal is included for comparison. The results shown seal diameter is unaffected by immersion in HFA 134a+10% propellant (with the exception of EF187~2B1). In comparison to the EPDM control, the compositions (with the exception of EF187/2) show equal or superior resistance to HFAs.

TABLE 1

Thermoplastic Elastomer Compositions

| Compound | Vistamaxx 1100 | Vistamaxx 1120 | Vistamaxx 2100 | Topas 8007 | Septon 2063 | Pebax 2533 | Mistron Vapor R10 C | Dokafill 600 |
|---|---|---|---|---|---|---|---|---|
| EF 185 | | | 80 | 20 | | | | |
| EF 186~2 | | | 60 | 20 | 20 | | | |
| EF187~2 | | | 80 | | | 20 | | |
| EF 192~2 | | 100 | | | | | 20 | |
| EF193~2 | | | 100 | | | | | 20 |
| EF194 | | 100 | | | | | | 10 |
| EF195 | | | 100 | | | | 40 | |
| EF196 | | | 80 | 20 | | | 10 | |
| EF197 | | | 60 | 20 | 20 | | 10 | |
| EF198 | | | 100 | | | | 20 | |
| EF199 | 100 | | | | | | 40 | |
| EF200 | | | 100 | | | | 60 | |
| EF201 | 100 | | | | | | 60 | |
| EF202 | 100 | | | | | | 20 | |

Vistamaxx1100: copolymer of isotactic propylene and alpha-olefin(s)
Vistamaxx1120: copolymer of isotactic propylene and alpha-olefin(s)
Vistamaxx 2100: copolymer of isotactic propylene and alpha-olefin(s)
Topas 8007: copolymer of cyclo-olefins
Pebax 2533: copolymer of polyether block polyamide
Septon 2063: styrene, ethylene, propylene, styrene block polymer
Mistron Vapor R10C: platy talc
Dokafill 600: clay filler

TABLE 2

Physical properties

| Sample | Batch number | MFI * (g/10 min) | Hardness shore A | Moisture (%) | Density (kg/m$^3$) | TS (N/mm$^2$) | E (100%) (N/mm$^2$) | E (200%) (N/mm$^2$) | E (300%) (N/mm$^2$) | $\epsilon_b$ (%) |
|---|---|---|---|---|---|---|---|---|---|---|
| EF 185 | 1 | 5.2 | 80 | 0.15 | 0.9 | 8.8 | 5.8 | 7.2 | 8.2 | 450 |
| EF 186~2 | 1 | 6.9 | 82 | 0.17 | 0.89 | 6.1 | 4.9 | 5.5 | 5.5 | 620 |
| EF187~2 | 1 | 10.8 | 69 | 0.22 | 0.89 | 10.9 | 3.3 | 3.8 | 4.3 | 940 |
| EF 192~2 | 1 | 8.8 | 70 | 0.12 | 0.97 | 9.5 | 3.1 | 3.6 | 4.1 | 790 |
| EF193~2 | 1 | 8.3 | 72 | 0.17 | 0.99 | 8.3 | 3.3 | 4.0 | 4.8 | 680 |
| EF194 | 1 | 8.5 | 68 | 0.15 | 1.05 | 9.7 | 2.9 | 3.4 | 4.1 | 800 |
| EF195 | 1 | 75 | 80 | 0.20 | 1.05 | 9.8 | 4.9 | 5.4 | 6.2 | 710 |
| EF196 | 1 | 6.8 | 74 | 0.15 | 0.92 | 10.7 | 6.6 | 8.1 | 9.4 | 480 |
| EF197 | 1 | 4.7 | 80 | 0.20 | 0.95 | 8.0 | 6.8 | 7.8 | 7.9 | 360 |
| EF198 | 1 | 7.9 | 75 | 0.20 | 0.99 | 8.6 | 4.0 | 4.6 | 5.4 | 630 |
| EF198 | 2 | 8.1 | 75 | 0.16 | 0.98 | 9.1 | 4.0 | 4.6 | 5.3 | 700 |
| EF199 | 1 | 1.7 | 80 | 0.10 | 1.08 | 11.6 | 5.5 | 6.4 | 7.0 | 600 |
| EF199 | 2 | 1.9 | 80 | 0.20 | 1.06 | 11.1 | 4.9 | 5.8 | 6.7 | 570 |
| EF200 | 1 | 5.5 | 82 | 0.19 | 1.18 | 9.5 | 5.4 | 6.0 | 6.8 | 640 |
| EF200 | 2 | 5.6 | 81 | 0.21 | 1.17 | 9.9 | 5.2 | 5.7 | 6.3 | 700 |
| EF201 | 1 | 1.6 | 80 | 0.15 | 1.16 | 11.7 | 5.4 | 6.4 | 7.4 | 590 |
| EF201 | 2 | 1.4 | 80 | 0.19 | 1.15 | 11.6 | 5.6 | 6.7 | 7.7 | 570 |
| EF202 | 1 | 1.9 | 73 | 0.17 | 0.99 | 10.4 | 4.1 | 5.0 | 5.8 | 580 |
| EF202 | 2 | 2.4 | 70 | 0.22 | 0.97 | 10.2 | 4.4 | 5.5 | 6.5 | 510 |

TABLE 3

Alloy compositions and GC-MS analysis

| | Alloys | | | | | | |
|---|---|---|---|---|---|---|---|
| | EF185 | EF186~2 | EP187~2 | EF192~2 | EF193~2 | EF194 | EF195 |
| Vistmaxx 1100 | — | — | | | | | |
| Vistamaxx 1120 | — | — | | 100 | | 100 | |
| Vistamaxx 2100 | 80 | 60 | 80 | | 100 | | 100 |
| Topas 8007 | 20 | 20 | | | | | |
| Pebax 2533 | — | — | 20 | | | | |
| Septon 2063 | — | 20 | | | | | |
| Mistron Vapor R10C | — | — | | 20 | | | 40 |

TABLE 3-continued

Alloy compositions and GC-MS analysis

| | | | | | | |
|---|---|---|---|---|---|---|
| Dokafill 600 | — | | | | 20 | 10 |
| GC-MS Analysis Of Alloys | 571 ppm | 389 ppm | 1102 ppm | 350 ppm | 133 ppm | |

GC-MS Analysis of a non ethanol EPDM rubber typically used in pMDI

| | |
|---|---|
| GC-MS Analysis Of EPDM rubber | 1874 ppm |

GC-MS Analysis of a non ethanol extracted Nitrile rubber typically used in pMDI

| | |
|---|---|
| GC-MS Analysis Of Nitrile rubber | 3146 ppm |

| | Alloys | | | | | | |
|---|---|---|---|---|---|---|---|
| | EF196 | EF197 | EF198 | EF199 | EF 200 | EF201 | EF202 |
| Vistmaxx 1100 | | | | 100 | | 100 | 100 |
| Vistamaxx 1120 | | | | | | | |
| Vistamaxx 2100 | 80 | 60 | 100 | | 100 | | |
| Topas 8007 | 20 | 20 | | | | | |
| Pebax 2533 | | | | | | | |
| Septon 2063 | | 20 | | | | | |
| Mistron Vapor R10C | 10 | 10 | 20 | 40 | 60 | 60 | |
| Dokafill 600 | | | | | | | 20 |
| GC-MS Analysis Of Alloys | | 314 ppm | 255 ppm | 6 ppm | | 22 ppm | 88 ppm |

GC-MS Analysis of a non ethanol EPDM rubber typically used in pMDI

GC-MS Analysis Of EPDM rubber

GC-MS Analysis of a non ethanol extracted Nitrile rubber typically used in pMDI

GC-MS Analysis Of Nitrile rubber

The invention claimed is:

1. A valve seal for use in a pharmaceutical dispensing device, wherein the seal comprises a sealing member formed from a seal material comprising a thermoplastic elastomer comprising a copolymer or terpolymer of propylene and one or more alpha-olefins selected from one or more of ethylene, butene, hexene, octene, and decene, wherein the propylene component constitutes at least 80% of the thermoplastic elastomer and at least a portion of the propylene component has isotactic crystallinity.

2. A valve seal as claimed in claim 1, wherein the propylene component has from 2 to 25% isotactic crystallinity.

3. A valve seal as claimed in claim 1, wherein the thermoplastic elastomer has a molecular weight (Mw) of at least 100,000.

4. A valve seal as claimed in claim 1, wherein the seal material comprises an additional thermoplastic component.

5. A valve seal as claimed in claim 4, wherein the additional thermoplastic component comprises one or more polymers selected from styrene-ethylene-ethylene-propylene, styrene-ethylene-propylene, styrene-butadiene-styrene, polyether block polyamide, polyether-polyester, ethylene-diene, polydimethylsiloxane/urea copolymers, and cyclo-olefin copolymers.

6. A valve seal as claimed in claim 4, wherein the one or more additional thermoplastic components is/are present in the seal material in an amount of from 1 to 40 wt. %.

7. A valve seal as claimed in claim 1, wherein the seal material further comprises a mineral and/or inorganic filler.

8. A valve seal as claimed in claim 7, wherein the filler is selected from one or more of clays, calcined clays, nano particle clays, talcs and amino-silane-coated clays.

9. A valve seal as claimed in claim 7, wherein the filler is present in the seal material in an amount of from 1 to 40 wt. %.

10. A valve seal as claimed in claim 1, wherein the seal material is essentially free of a cross-linking agent.

11. A valve seal as claimed in claim 1, wherein the seal material is essentially free of a plasticizer.

12. A valve seal as claimed in claim 1, wherein the seal material is essentially free of a processing aid.

13. A valve seal as claimed in claim 1, wherein the seal material is essentially free of a compatiblising agent.

14. A valve for use in a pharmaceutical dispensing device having a seal, wherein the seal is formed from a material comprising a thermoplastic elastomer comprising a copolymer or terpolymer of propylene and one or more alpha-olefins selected from one or more of ethylene, butene, hexene, octene, and decene, wherein the propylene component constitutes at least 80% of the thermoplastic elastomer and at least a portion of the propylene component has isotactic crystallinity.

15. A pharmaceutical dispensing device having a valve, wherein the valve comprises a seal, wherein the seal is formed from a material comprising a thermoplastic elastomer comprising a copolymer or terpolymer of propylene and one or more alpha-olefins selected from one or more of ethylene, butene, hexene, octene, and decene, wherein the propylene component constitutes at least 80% of the thermoplastic elastomer and at least a portion of the propylene component has isotactic crystallinity.

16. A pharmaceutical dispensing device as claimed in claim 15 which is a pharmaceutical metered dose aerosol inhaler device.

17. A dispensing apparatus for dispensing pressurised fluid comprising a valve body defining a chamber, a valve member extending movably through the chamber and through at least one annular seal co-operating with the valve member and the body to regulate the discharge of fluid, wherein the at least one seal is formed from a material comprising a thermoplastic elastomer comprising a copolymer or terpolymer of propylene and one or more alpha-olefins selected from one or more of ethylene, butene, hexene, octene, and decene, wherein the propylene component constitutes at least 80% of the thermoplastic elastomer and at least a portion of the propylene component has isotactic crystallinity.

18. A dispensing apparatus comprising a pressurised dispensing container having a valve body provided with two annular valve seals through which a valve member is axially slidable, said seals being disposed at inlet and outlet apertures of a valve chamber so that the valve functions as a metering valve, wherein at least one of the annular valve seals is formed from a material comprising a thermoplastic elastomer comprising a copolymer or terpolymer of propylene and one or more alpha-olefins selected from one or more of ethylene, butene, hexene, octene, and decene, wherein the propylene component constitutes at least 80% of the thermoplastic elastomer and at least a portion of the propylene component has isotactic crystallinity.

19. A dispensing apparatus as claimed in claim 17, comprising a pressurised dispensing container operatively connected to the valve body and containing the fluid to be dispensed and a hydrofluorocarbon propellant comprising propellant type 134a or 227.

20. A dispensing apparatus as claimed in claim 17, wherein the fluid to be dispensed comprises a liquid or particulate product as a solution or suspension in a carrier liquid comprising alcohol.

21. A dispensing apparatus as claimed in claim 20, wherein the alcohol comprises ethanol.

22. A valve seal as claimed in claim 2, wherein the propylene component has from 5 to 15% isotactic crystallinity.

23. A valve seal as claimed in claim 6, wherein the one or more additional thermoplastic components is/are present in the seal material in an amount of from 1 to 10 wt. %.

24. A valve seal as claimed in claim 9, wherein the filler is present in the seal material in an amount of from 1 to 30 wt. %.

* * * * *